US009844258B2

(12) United States Patent
Trebella et al.

(10) Patent No.: US 9,844,258 B2
(45) Date of Patent: Dec. 19, 2017

(54) ASSISTIVE DEVICE FOR A MICROBIAL SCRUB BRUSH

(75) Inventors: Matthew Trebella, Stansbury Park, UT (US); Russell L. Bjorklund, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 462 days.

(21) Appl. No.: 13/111,518

(22) Filed: May 19, 2011

(65) Prior Publication Data

US 2011/0284024 A1 Nov. 24, 2011

Related U.S. Application Data

(60) Provisional application No. 61/346,650, filed on May 20, 2010.

(51) Int. Cl.
| | | |
|---|---|---|
| *B08B 1/04* | (2006.01) | |
| *B08B 1/00* | (2006.01) | |
| *A46B 13/04* | (2006.01) | |
| *B08B 7/00* | (2006.01) | |
| *B08B 9/02* | (2006.01) | |
| *A61B 90/70* | (2016.01) | |

(52) U.S. Cl.
CPC ............ *A46B 13/04* (2013.01); *A61B 90/70* (2016.02); *B08B 1/002* (2013.01); *B08B 7/0057* (2013.01); *B08B 9/021* (2013.01)

(58) Field of Classification Search
CPC ......... A46B 13/001; A46B 7/04; A46B 13/00; A46B 2200/3013; A46B 13/04; B08B 9/021; B08B 7/0057; B08B 1/002; A61B 90/70

USPC ......... 15/21.1, 22.1, 88, 104.04, 143.1, 145, 15/176.1, 176.2
See application file for complete search history.

(56) References Cited

U.S. PATENT DOCUMENTS

| | | | | |
|---|---|---|---|---|
| 4,301,567 | A | * | 11/1981 | Tucker ..................... A46B 7/04 15/104.04 |
| 5,078,158 | A | * | 1/1992 | Lemon et al. ................ 132/200 |
| 5,094,556 | A | * | 3/1992 | Kohler ..................... A46B 9/02 15/106 |
| 5,373,599 | A | * | 12/1994 | Lemon et al. ............. 15/104.94 |

(Continued)

FOREIGN PATENT DOCUMENTS

WO    2011146730 A1    11/2011

OTHER PUBLICATIONS

PCT/US11/37176 filed May 19, 2011 International Search Report dated Sep. 12, 2011.

(Continued)

*Primary Examiner* — Douglas Lee
(74) *Attorney, Agent, or Firm* — Rutan & Tucker, LLP

(57) ABSTRACT

A system and device for assisting with the cleansing of a medical component with a scrub brush is disclosed. In one embodiment, an assistive device for use with the scrub brush is disclosed. The scrub brush includes an insert disposed therein, the insert including a cleansing substance such as CHG or alcohol. The assistive device comprises a housing, a motor, a head removably supporting the scrub brush, and an interface interconnecting the motor and the head. The interface is a shaft that enables back-and-forth rotation or other movement of the head and scrub brush relative to the medical component so as to cleanse the medical component.

20 Claims, 7 Drawing Sheets

(56) References Cited

U.S. PATENT DOCUMENTS

| | | | |
|---|---|---|---|
| 5,474,075 A * | 12/1995 | Goldberg | A61B 8/12 600/463 |
| 5,735,013 A * | 4/1998 | Yaguchi | B08B 1/008 15/104.04 |
| 6,047,431 A | 4/2000 | Canonica | |
| 6,099,309 A * | 8/2000 | Cardarelli | 433/125 |
| 6,527,552 B2 * | 3/2003 | Loddeke et al. | 433/125 |
| 6,611,780 B2 * | 8/2003 | Lundell | A61C 17/22 433/27 |
| 6,821,119 B2 * | 11/2004 | Shortt | A61C 17/22 433/118 |
| 6,902,397 B2 * | 6/2005 | Farrell | B08B 7/0057 15/167.1 |
| 7,476,885 B2 * | 1/2009 | Garcia | A61L 2/10 15/339 |
| 2004/0019990 A1 | 2/2004 | Farrell et al. | |
| 2004/0255414 A1 * | 12/2004 | Tulipana | B08B 1/04 15/104.04 |
| 2006/0210948 A1 * | 9/2006 | Rose et al. | 433/125 |
| 2006/0292522 A1 * | 12/2006 | Lees et al. | 433/116 |
| 2007/0154863 A1 * | 7/2007 | Cai et al. | 433/89 |
| 2007/0254260 A1 * | 11/2007 | Alden | A46B 15/0055 433/85 |
| 2008/0034515 A1 | 2/2008 | Hilscher et al. | |
| 2008/0155769 A1 | 7/2008 | Schonewille et al. | |
| 2008/0235888 A1 | 10/2008 | Vaillancourt et al. | |
| 2009/0038639 A1 * | 2/2009 | Yetukuri | A46B 15/0002 134/6 |
| 2009/0226241 A1 | 9/2009 | McEwen et al. | |
| 2010/0072399 A1 * | 3/2010 | Street | A61L 2/10 250/492.1 |
| 2010/0200017 A1 | 8/2010 | Kerr et al. | |
| 2011/0030726 A1 | 2/2011 | Vaillancourt et al. | |

OTHER PUBLICATIONS

PCT/US11/37176 filed May 19, 2011 Written Opinion dated Sep. 12, 2011.

* cited by examiner

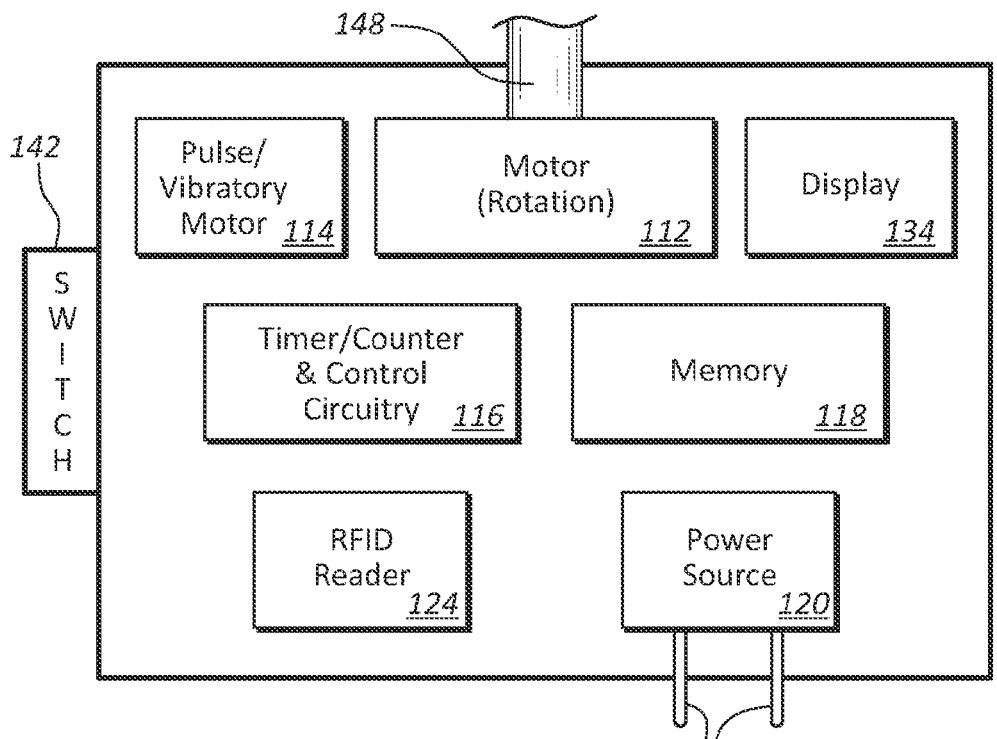
FIG. 1A
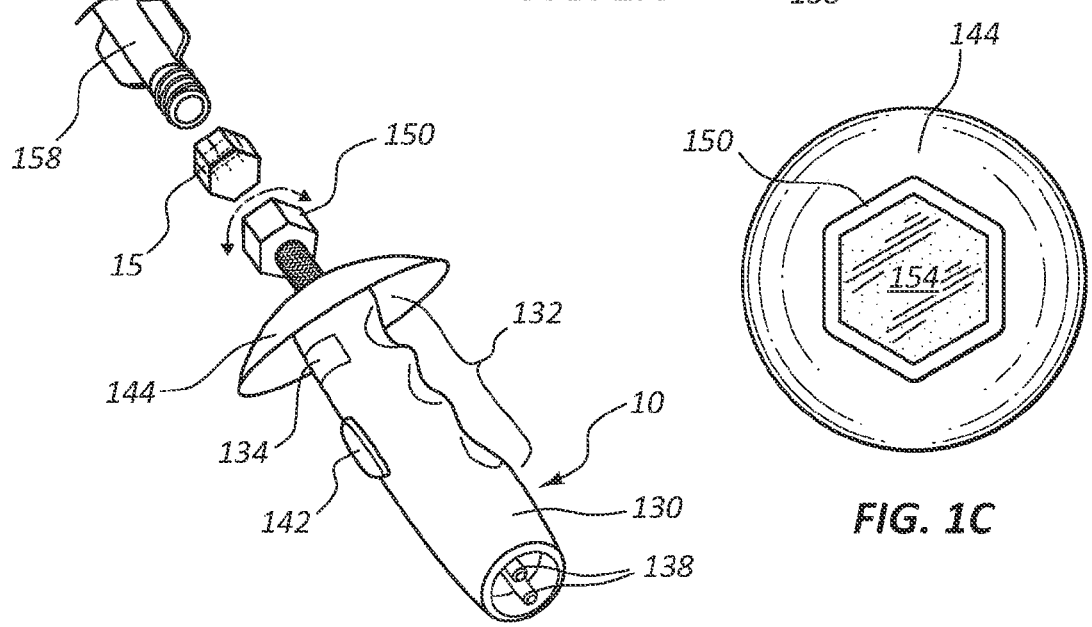
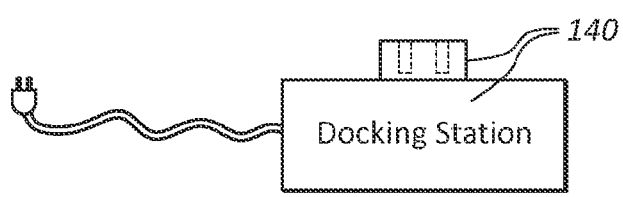
FIG. 1C
FIG. 1B

ASSISTIVE DEVICE FOR A MICROBIAL SCRUB BRUSH

CROSS-REFERENCE TO RELATED APPLICATIONS

This application claims the benefit of U.S. Provisional Patent Application No. 61/346,650, filed May 20, 2010, and entitled "Assistive Device for Use with a Microbial Scrubbing Device," which is incorporated herein by reference in its entirety.

BRIEF SUMMARY

Briefly summarized, embodiments of the present invention are directed to a system and device for assisting with the cleansing of a medical component with a scrub brush. In one embodiment, an assistive device for use with the scrub brush is disclosed. The scrub brush includes an insert disposed therein, the insert including a cleansing substance such as CHG or alcohol. The assistive device in one embodiment comprises a housing, a motor, a head removably supporting the scrub brush, and an interface interconnecting the motor and the head. The interface is a shaft that enables back-and-forth rotation or other movement of the head and scrub brush relative to the medical component so as to cleanse the medical component.

In addition, other modalities are included in the assistive device, such as ultrasonic pulsing, vibratory motion, and vacuum assistance, to enhance cleansing action. In one embodiment, a docking station is included to charge a rechargeable battery of the assistive device and to download useful information relating to its operation. In yet another embodiment, multi-unit scrub brushes are disclosed for use with the assistive device.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 1A is a simplified block diagram of an assistive device for a microbial scrub brush according to one embodiment;

FIG. 1B is a perspective view of a cleansing system for cleansing a connector or other portion of a medical device, according to one embodiment;

FIG. 1C is an end view of the assistive device of FIG. 1B;

DETAILED DESCRIPTION OF SELECTED EMBODIMENTS

Figure 2A:
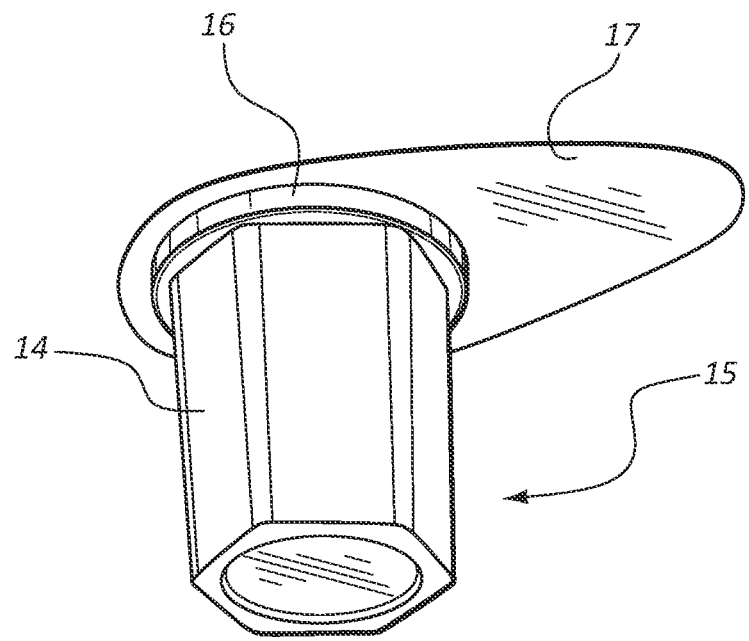
FIGS. 2A and 2B are perspective and top views, respectively, of a scrub brush device for use with the system of FIG. 1B according to one embodiment.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a system and device for assisting with the cleansing of a medical component or a portion of a medical device, such as a luer connector of a catheter, for instance. In one embodiment, the system includes a scrubbing device, or scrub brush, which contains a cleansing substance and is useful for engaging and cleansing interior and exterior surfaces of the medical component.

A handheld assistive device is also included with the system and is configured to operably attach to the scrub brush. The assistive device in one embodiment includes a rotatable head in which the scrub brush is received. This enables the scrub brush to be selectively rotated relative to the medical component after engagement thereof in order to ensure that the component is suitably cleansed by the scrubbing device. In one embodiment, the assistive device is powered to rotate the scrubbing device about the medical component in a back-and-forth rotating motion a predetermined number of times or for a selected amount of time so as to ensure suitable cleansing of the component by the scrub brush.

Reference is first made to FIGS. 1A-1C in describing details regarding an assistive cleaning device 10 and related system according to one embodiment. As shown, the assistive device ("device") 10 is configured in the present embodiment as a handheld device for use by a clinician or other user to assist in using a scrub brush 15 to clean a medical component, such as a hub 158, as will be described in further detail below.

FIG. 1A depicts various components included in the device 10 according to one embodiment. A motor 112 is included for providing rotational movement to a shaft 148. In addition, in one embodiment a vibratory motor component 114 can be included to provide pulse or vibration to the device 10. Control circuitry 116 including a timer and/or counter circuit is included to control device functionality. A memory module 118 is included for tracking usage statistics of the device 10.

A power source 120 is included and can include a rechargeable battery or other suitable source for driving operation of the device 10. In the present embodiment, the power source 120 includes a rechargeable battery that can be charged via a docking station 140 (FIG. 1B). Contacts 138 are included on the device 10 to enable operable connection between the power source 120 and the docking station 140 so as to charge the device battery. In other embodiments the power source can be plugged in to a wall outlet or can include disposable batteries, for instance.

Figure 5:
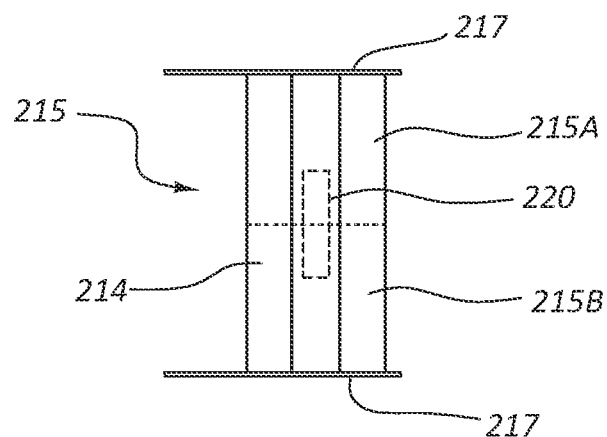
FIG. 5 is a side view of a multi-unit scrub brush configured according to one embodiment.

In one embodiment, an RFID reader 124 is included to enable the device 10 to detect and read information present on an RFID chip included in a scrub brush, such as the chip 220 included in the scrub brush 215 shown in FIG. 5. Further details regarding this will be given below.

Further details regarding the assistive device 10 according to the present embodiment are depicted in FIG. 1B. As shown, the device 10 includes a housing 130 configured for handheld use by a clinician. A gripping surface 132 is included to assist with grasping the device 10 during use. A display 134 is included to depict information regarding use of the device 10, such as the number of rotations performed, the amount of time the device has been used, etc. The information displayed can be cumulative or relating to a present cleaning cycle. In one embodiment, control buttons are included to control functionality of the display 134.

A switch 142 is included on the housing 130 to enable activation of the device 10 in the manner described further below. The switch 142 may included simple on/off functionality, and optionally may include the ability to switch between different modes, such as rotation, vibration, etc. Additional control switches/buttons can be employed to control various aspects of device operation. The device 10 further includes in the present embodiment a plurality of contacts 138 included with the housing 130 to enable the device to be operably connected to the docking station 140 so as to enable charging of a rechargeable battery, internally included as the device power source 120 (FIG. 1A).

A shaft 148 extends from the housing 130 and is operably connected to the motor 112 (FIG. 1A) included within the housing. The shaft 148 has attached thereto a rotational head 150 that supports a scrub brush 15. The scrub brush is configured to engage a medical component, such as a connector or hub 158 of a catheter, so as to cleanse the component in the manner described further below. The head 150 can be permanently attached to the shaft 148, or removably attached so as to enable cleansing/replacement of the head to ensure the cleanliness thereof. A shield 144 is included proximate the shaft 148 so as to reduce the possibility of contamination from the scrub brush reaching the hand of the user on the device 10. The shield 144 can be configured in multiple ways.

Figure 2B:
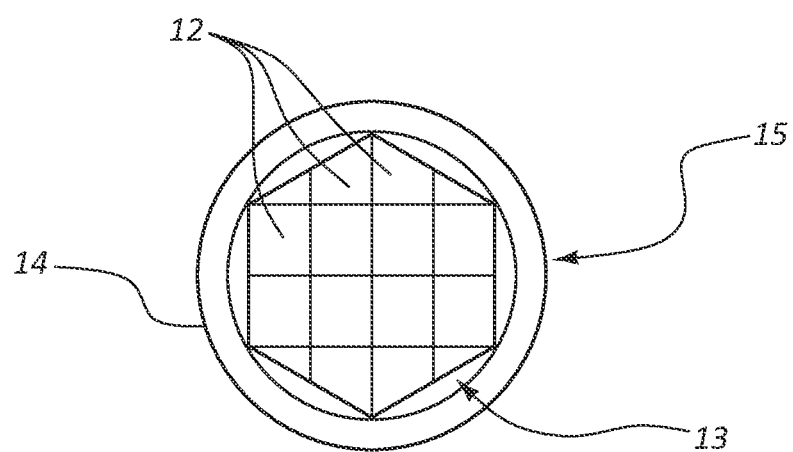

As best seen in FIG. 1C, the head 150 defines a socket-like receptacle 154 shaped to receive the scrub brush 15 therein. In particular, FIGS. 2A and 2B show that the scrub brush 15 includes a holder 14 defining a lip 16. The holder 14 defines a hexagonal shape, though other holder shapes are, of course, possible. Correspondingly, the receptacle 154 of the head 150 is hexagonally shaped so as to snugly receive therein the scrub brush 15. The receptacle 150 is sized so that a slight friction fit is achieved when the holder 14 is inserted therein, thus retaining the scrub brush 15 in place within the receptacle. In other embodiments, interengaging features can be included in the receptacle and the scrub brush/holder so that engagement between the receptacle and the scrub brush is maintained.

FIGS. 2A and 2B depict further details regarding the scrub brush 15. An insert 13 defining a plurality of digitated fingers 12 is disposed within a cavity defined by the holder 14. The fingers 12 of the insert 13 are configured to physically engage external and internal surfaces of a medical component, such as the catheter hub 158, so as to remove microbes, biofilm, etc. therefrom. In the present embodiment, a suitable cleansing substance including chlorhexidine gluconate ("CHG") and/or isopropyl alcohol ("IPA") for instance, is included with the insert 13 and fingers 12 within the cavity of the scrubbing device holder 14 to assist in the cleansing process. Further details regarding the scrub brush can be found, for instance, in U.S. Patent Application Publication No. 2010/0200017, entitled "Microbial Scrubbing Device," filed Apr. 1, 2010, and U.S. Patent Application Publication No. 2011/0030726, entitled "Insert for a Microbial Scrubbing Device," filed Aug. 20, 2010, each of which is incorporated herein by reference in its entirety. In addition to the description given herein, it is appreciated that the scrub brush and its insert can be configured in other ways, including differing finger types, cleansing solutions, holder shapes, etc.

Figure 3:
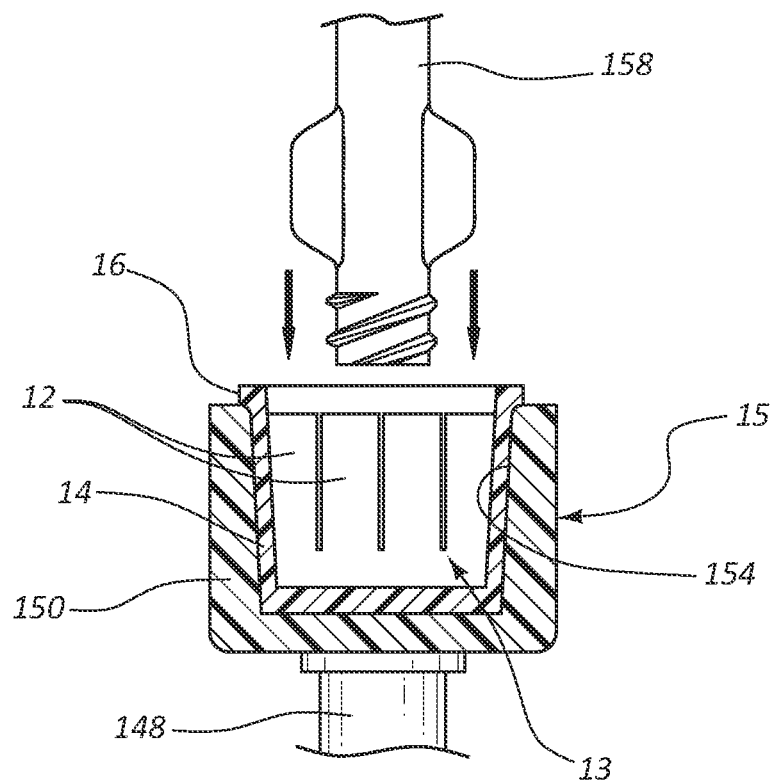
FIGS. 3 and 4 show engagement of a catheter connector with the scrub brush and assistive device of FIG. 1B.
Figure 4:
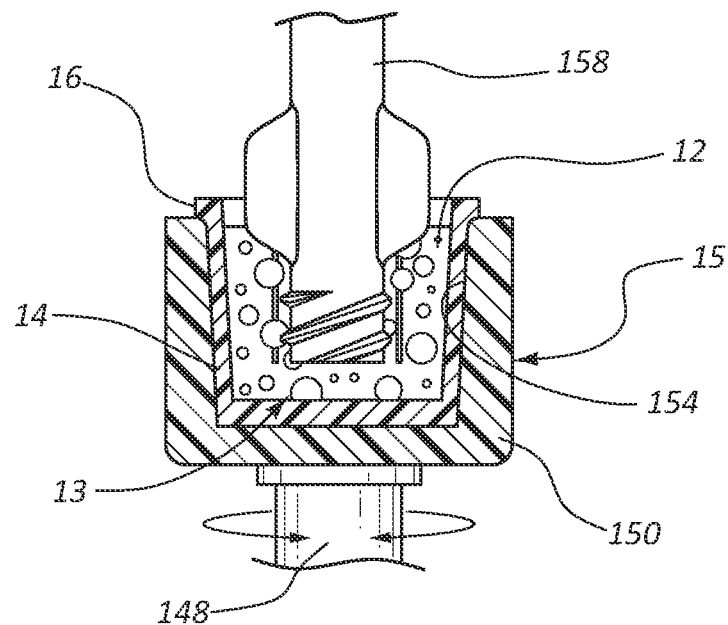

Reference is now made to FIGS. 3 and 4 in describing operation of the device 10 is assisting with cleansing of the hub 158 or other medical component with the scrub brush 15. As shown, at the initiation of a cleansing procedure the scrub brush 15 is loaded into the head 150 of the device 10 by inserting it into the head receptacle 154, as seen in FIG. 3. So positioned, the lip 16 of the scrub brush extends above the entrance to the head receptacle 154, though other positional configurations are possible. The device user then positions the device and connected scrub brush 15 such that the hub 158 is received into the cavity of the scrub brush holder 14. This causes the fingers 12 of the insert 13 to engage both external and internal surfaces of the hub 158, as seen in FIG. 4.

At this stage, the device 10 can be activated to rotate the head 150 (via the shaft 148) and the scrub brush 15 received therein relative to the hub 158, all while the housing 130 is held stationary by the user. In the present embodiment, the device 10 causes back- and forth rotational movement of the scrub brush relative to the hub 158. In other embodiments, simple rotation in one or both circular directions (i.e., clockwise, counter-clockwise) or other suitable movements can be executed by the device 10.

In one embodiment, the scrub brush 15 is moved relative to the connector for a predetermined number of back-and-forth rotational cycles, such as eight for instance, to cleanse exterior and interior surfaces of the hub 158 (FIG. 4). In another embodiment, the scrub brush is moved for a predetermined amount of time or revolutions, and at one or more rotational/directional speeds. Such parameters can be predisposed in or user-programmed into the control circuitry 116. Information relating to scrub brush movement can be depicted on the display 134 to assist the user during the cleansing process. Again, control buttons in addition to the features of the device 10 shown in FIG. 1B can be included to control functionality of the device during use. The resultant scrubbing of the hub 158 by the fingers 12 and included cleansing solution of the scrub brush insert 13 results in removal of biofilms or other impurities or microbes from the hub, resulting in cleansing thereof.

In one embodiment, the pulse/vibratory motor 114 (FIG. 1A) of the device 10 can be selectively or automatically activated to introduce vibration to the scrub brush 15/hub 158 connection so as to further assist in hub cleansing.

Use of the device 10 to move the scrub brush 15 relative to the hub 158 negates the need for a nurse or other clinician to manually rotate the scrub brush, thus easing the cleansing process and reducing user fatigue, especially when many such connectors must be cleansed by a nurse or clinician during a work shift. Moreover, use of the device can take guesswork out determining when a medical component has been cleansed for a sufficient number of cycles or amount of time. Of course, in one embodiment the device can be configured to rotate/move the head continuously when the device switch is on.

In another embodiment, the device can include a visual and/or audible indicator for alerting the clinician when a sufficient amount of cleansing (by time, rotation, or other measurement) has been performed. In this case, the visual and/or audible indicator (e.g., light and sound speaker) can be operably connected to the timer/counter control circuitry 116, which controls indicator activation.

In addition to what is shown herein, the housing of the device can be shaped in one of many ergonomic or other suitable shapes for handheld use, and the device can be adapted for use with a holster, lanyard, etc. for ease of transport. In one embodiment, the assistive device can be configured to move the head and included scrub brush axially with respect to the catheter connector for enhanced cleansing, in addition or as opposed to the radial movement described above. In another embodiment, it is anticipated that the device can include an eject mechanism for selectively popping the scrub brush out of the receptacle of the head when the scrub brush is ready for disposal, thus averting possible contact with impurities present in the scrub brush after use. In another embodiment, it is appreciated that the assistive device can include more than one rotational head. For instance, the device can include first and second heads, where each head is configured to connect with a scrub brush. This enables a single assistive device to clean more than one medical component at a time.

As mentioned, the shapes of both the scrub brush holder 14 and the receptacle 154 of the rotational head 150 of the device 10 are hexagonal in the illustrated embodiment, though it is appreciated that other corresponding shapes can be used for these components. In addition, other manners of engagement between the scrub brush and the assistive device head (e.g., adhesively, via hook-and-loop fabric (e.g., VELCRO), friction, magnets) can be employed.

As mentioned, in one embodiment and as shown in FIG. 1B, the docking station 140 can be included in the system to enable charging of the assistive device 10, but also to enable downloading of use/performance/RFID data captured by the assistive device in its memory 118 (FIG. 1A), etc. Also in one embodiment, the rotational head of the device can be removable so as to be sterilized, or can be disposable.

FIGS. 5-10B disclose various scrub brush configurations according to example embodiments, at least some of which can be employed with the assistive device 10 of FIGS. 1A and 1B. FIG. 5 shows a dual scrub brush 215 including joined and linearly opposed scrub brush portions 215A, B included in a holder 214. As in the other embodiments, the opening to the cavity of each portion 215A, B is covered by a removable cover 217. This and the other multiple scrub brush configurations herein can be employed in one embodiment to facilitate cleansing more than one connector in a single cleansing session, for instance, and also provide the operator with a mechanical advantage for cleansing the medical device via a relatively larger holder. That is, these configurations in one embodiment make it easier to spin the scrub brush and reduce the amount of time needed to clean the medical component(s).

The multiple scrub brush 215 also includes an RFID chip 220 including information regarding the scrub brush itself. This in turn enables RFID-based tracking by the RFID reader 124 of the device 10 (FIG. 1A), such as how many scrub brushes have been used with the device, time of use for each RFID-equipped scrub brush, the number of rotations/cycles each scrub brush was subjected to, etc. Such information can be stored in the memory 118 of the device 10 for later download via the docking station 140 or other suitable route (e.g., wirelessly). In addition, the assistive device 10 can be configured in one embodiment to measure/record data relating to operation of the device, including torque, pressure monitoring to ensure good engagement between the rotational head and the scrub device, etc. Note generally that an RFID chip can be included in any one of the scrub brush configurations shown, described, and/or contemplated herein.

Figure 6:
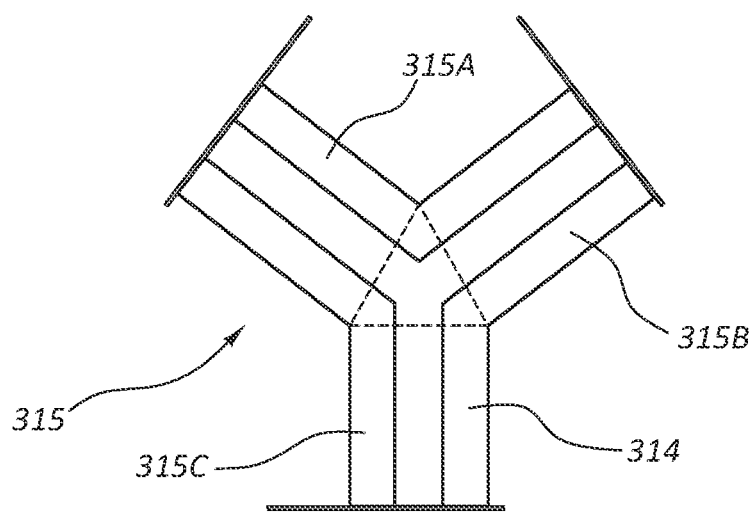
FIG. 6 is a side view of a multi-unit scrub brush configured according to one embodiment.
Figure 7:
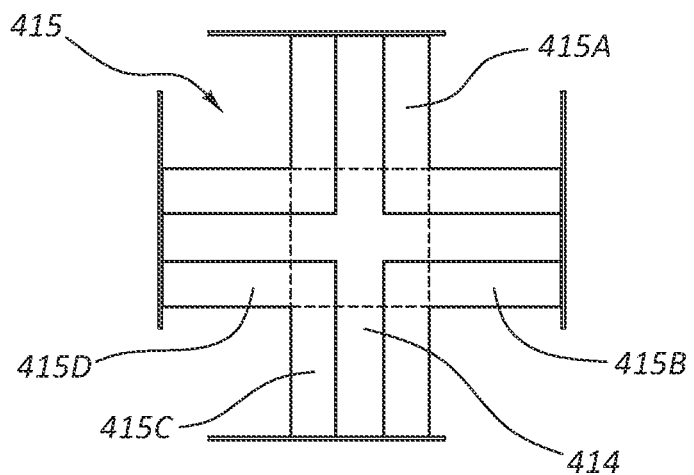
FIG. 7 is a side view of a multi-unit scrub brush configured according to one embodiment.

FIG. 6 shows a three-way scrub brush 315, with a holder 314 including scrub brush portions 315A, B, C joined in a planar, Y-shaped configuration. FIG. 7 shows a four-way scrub brush 415 with a holder 414 including scrub brush portions 415A, B, C, D in a planar, cross-shaped configuration.

Figure 8:
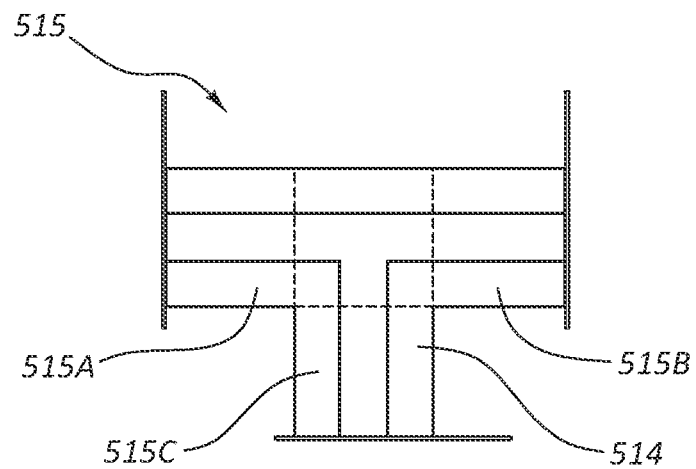
FIG. 8 is a side view of a multi-unit scrub brush configured according to one embodiment.
Figure 9:
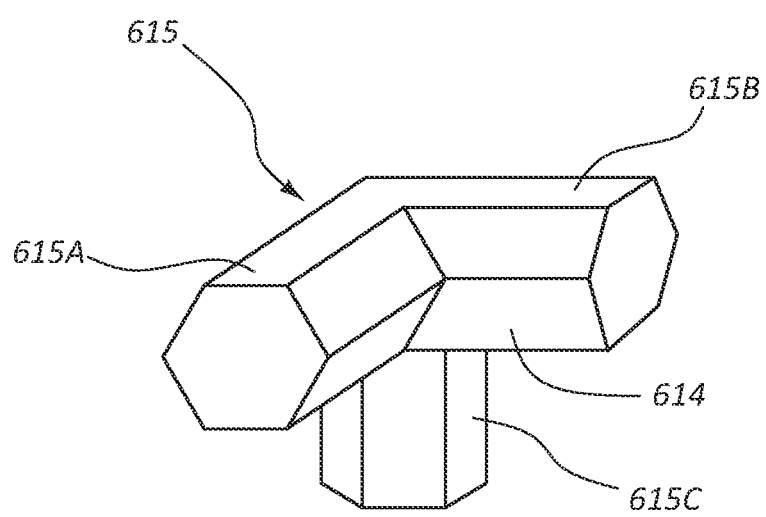
FIG. 9 is a perspective view of a multi-unit scrub brush configured according to one embodiment.

FIG. 8 shows another three-way scrub brush 515 with a holder 514 including scrub brush portions 515A, B, C joined in a planar, T-shaped configuration. FIG. 9 shows a multi-scrub brush 615 with a holder 614 including three scrub brush portions 615A, B, C joined in an orthogonal axis configuration.

Figure 10A:
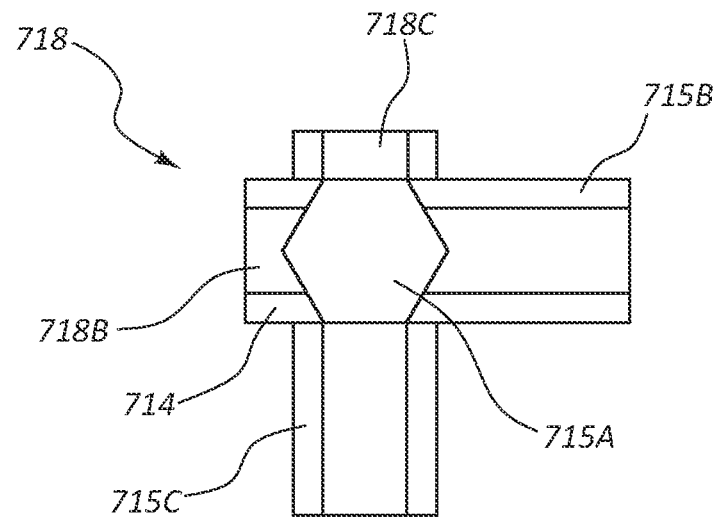
FIGS. 10A and 10B are side and perspective views, respectively, of a multi-unit scrub brush configured according to one embodiment.
Figure 10B:
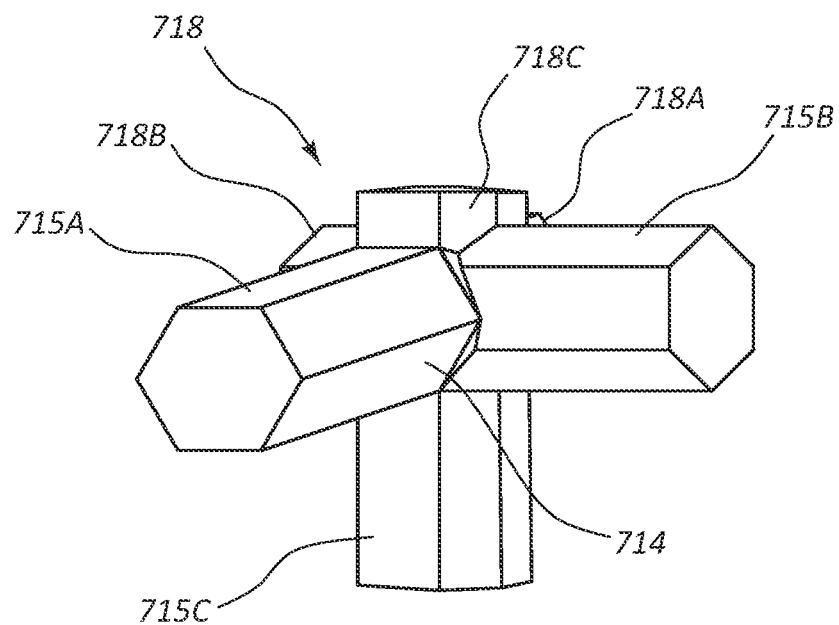

FIGS. 10A and 10B show a three-way orthogonal scrub brush 715 with a holder 714 including scrub brush portions 715A, B, C, and further including opposing engagement nubs 718A, B, C. The engagement nubs 718A, B, C respectively correspond to the scrub brush portions 715A, B, C and are opposingly aligned therewith to enable nub engagement with the receptacle 154 of the head 150 of the device 10. This enables any one of the scrub brush portions 715A, B, C to be selectively rotated by the assistive device 10, as described above. Note that the above principles can be expanded to multi-scrub brush configurations including other numbers of scrub brush portions.

Figure 11:
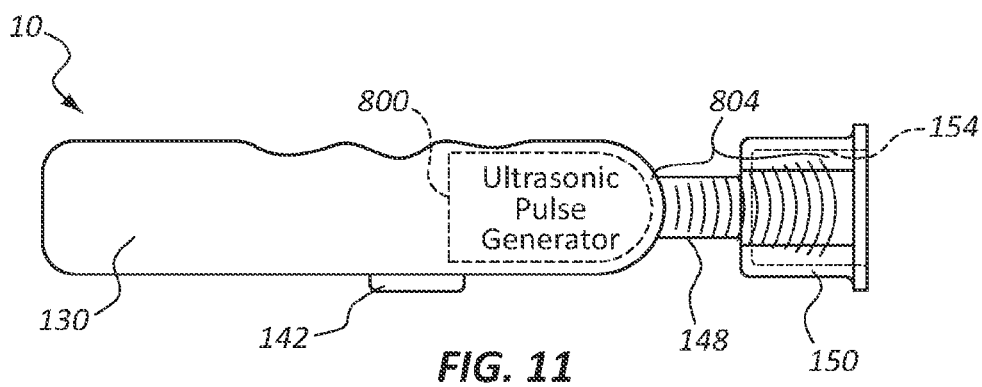
FIG. 11 is a side view of an assistive device for a microbial scrub brush according to one embodiment.

The assistive device can include additional or other cleansing modalities as well. For instance, in one embodiment shown in FIG. 11 the assistive device 10 includes an ultrasound pulse generator 800 for generating ultrasonic pulses 804 that are transferred to the scrub brush insert 13 during use of the device and scrub brush 15. The ultrasonic pulses 804 assist with penetration of the cleansing solution and disruption/destruction of microbes and biofilm by the insert fingers 12. In this way, ultrasonic pulsing is combined with rotational scrubbing by the scrub brush 15 to cleanse the connector or other medical device. It is appreciated that ultrasonic pulsing can be achieved in other ways. For instance, the rotational head of the assistive device can produce the ultrasonic pulses for cleansing in lieu of transmitting the pulses through the head from the housing. In yet another embodiment, crystals or other suitable structures for producing ultrasonic pulsing can be included in the scrub brush itself. These and other modifications are therefore contemplated.

Figure 12A:
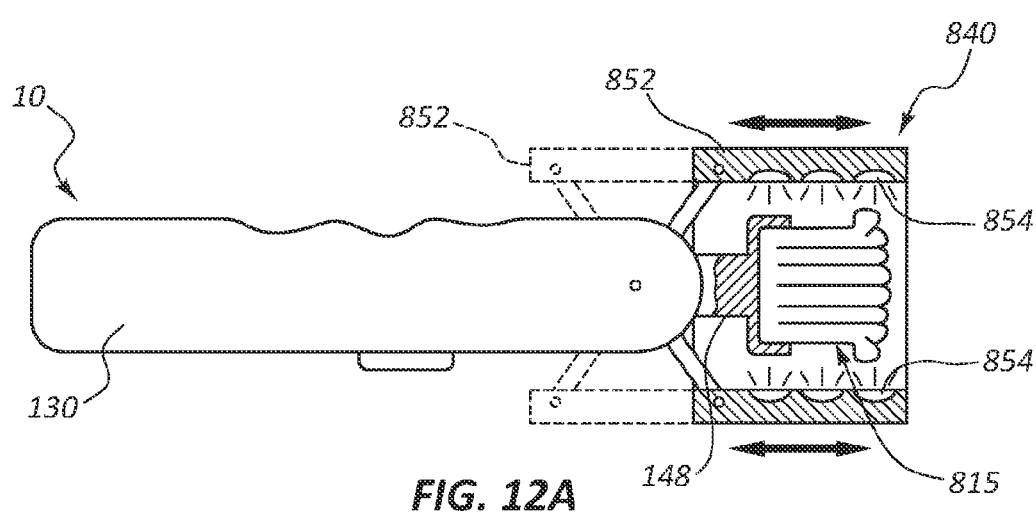
FIGS. 12A and 12B are side and end views, respectively, of an assistive device for a microbial scrub brush according to one embodiment.
Figure 12B:
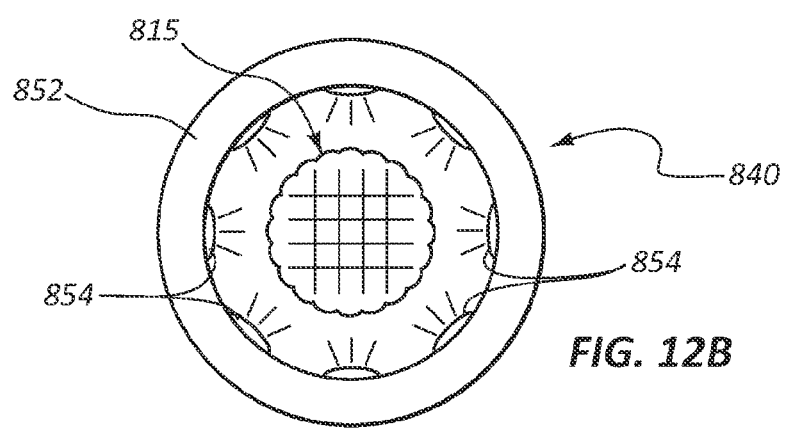

FIGS. 12A and 12B depict yet another cleansing modality, wherein an ultraviolet ("UV") light system 840 is included with the assistive device 10. As shown, a rotational head 850 is configured to receive a scrub brush 815, and is operably attached to the shaft 148. The scrub brush 815 includes no holder as in previous embodiments, but rather includes an insert defining a plurality of fingers.

A cylinder 852 is attached to the housing 130 of the device 10 so as to surround the scrub brush 815 attached to the head 850. The cylinder 852 includes a plurality of inward-facing ultraviolet-emitting ("UV") lights, such as LEDs 854, which are configured to direct UV light toward the scrub brush 815 and the medical component engaged therewith during cleansing. Impingement of the UV light on the scrub brush 815 and engaged medical component enables the UV light to penetrate and kill microbes and biofilm present on the medical component and scrub brush.

As shown, the cylinder 852 is attached to the housing 130 of the device so as to be axially slidable. This enables the cylinder 852 to be slid away from the head 850 to enable insertion/removal of the scrub brush 815. The present embodiment thus provides two-stage cleansing via the scrubbing action of the scrub brush and cleansing solution together with the UV light-based cleansing. It is appreciated that the shape and configuration of the UV light structure can vary from what is described herein.

Figure 13:
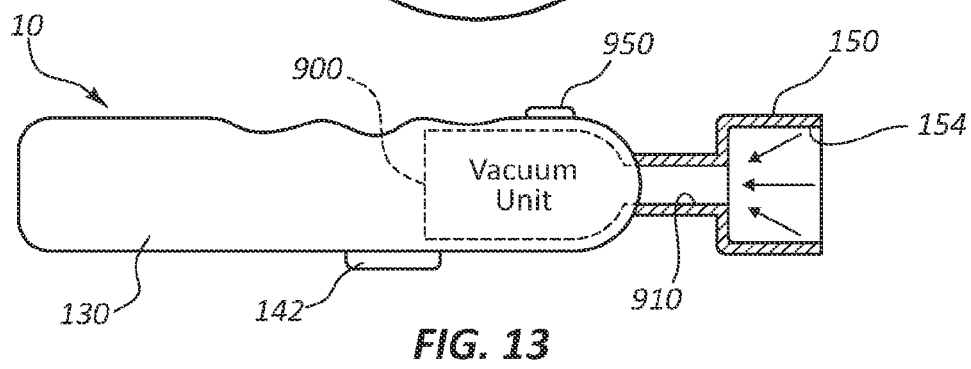
FIG. 13 is a side view of an assistive device for a microbial scrub brush according to one embodiment.

FIG. 13 depicts the assistive device 10 according to another embodiment, wherein a vacuum unit 900 is included within the device housing 130. A conduit 910 is defined between the vacuum unit and the receptacle 154 of the head 150 such that a negative pressure can be selectively imposed on the receptacle when the vacuum unit is activated. A scrub brush including a hole in the base of the holder can be inserted into the receptacle 154. So configured, a negative pressure can be established in the insert of the scrub brush via the hole in the holder and the conduit 910 to the vacuum unit when activated. This negative pressure in the scrub brush insert enables biofilm and other matter removed by the scrub brush during cleansing of the medical component to be captured and retained by the insert, thus preventing the matter from re-contaminating the medical component or, in the case of a catheter for example, from being inadvertently introduced into a lumen of the catheter and into the body of a patient. In this way, the insert of the scrub brush acts as a filter in capturing the removed matter. The vacuum unit 900 source can take one of many forms, and the conduit/scrub brush interface be configured in a variety of suitable ways in addition to what is shown here.

FIG. 13 further shows that in one embodiment, the assistive device 10 can further include an input device, such as a barcode scanner 950, to input patient information into the memory 118 (FIG. 1A) of the assistive device. This enables information relating to operation of the assistive device 10 to be linked to a particular patient when that patient's identifying information is scanned by the barcode scanner 950 and thus input into the device as part of a cleansing process. The linked information can be stored by the device memory 118 (FIG. 1A) and later downloaded to the docking station 140 (FIG. 1B) or in another suitable way. In one embodiment, RFID info. relating to one or more scrub brushes as contained in an RFID chip of the scrub brush can also be linked to a particular patient in this manner so as to provide a cleansing record, including for example the time, date, number of cleansing cycles and scrub brushes used during the cleansing process, etc. The cleansing record can be downloaded to the docking station 140 or in another suitable way for later use. Note that, in addition to a barcode scanner, other possible input devices that can be included on the assistive device for use include a keyboard, camera, etc.

It should be appreciated that, notwithstanding the above discussion, the relative shapes and sizes of the scrub brush, the medical component, and the assistive device can vary from what is shown and described herein while still residing within the scope of the present disclosure.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An assistive device for use of at least one scrub brush in cleansing a medical component, the scrub brush being structured to fit around an end and sides of the medical component and including an insert disposed therein, the insert including a cleansing substance, the assistive device comprising:
   a housing;
   a motor;
   at least one head removably supporting the scrub brush such that walls of the at least one head are in contact with and surround a majority of the scrub brush when the scrub brush is supported in the at least one head;
   an interface interconnecting the motor and the head to enable movement of the head and scrub brush relative to the medical component when the medical component is engaged with the scrub brush so as to cleanse the medical component; and
   an ultraviolet light system attached to the housing and includes a plurality of ultraviolet-emitting lights that can direct ultraviolet light radially inwardly toward the scrub brush and the medical component when the scrub brush is engaged in cleansing the medical component.

2. The assistive device as defined in claim 1, wherein the interface includes a shaft rotatably attached to the motor, wherein the scrub brush includes an outer holder defining an outer shape, and wherein the head supporting the scrub brush includes a receptacle correspondingly shaped with respect to the outer holder so as to receive therein the scrub brush.

3. The assistive device as defined in claim 1, further comprising at least one of the plurality of ultraviolet lights is disposed on a support structure so as to impinge ultraviolet light on the medical component when received by the scrub brush.

4. The assistive device as defined in claim 1, wherein the interface is a shaft, the shaft providing at least one of vibratory and back-and-forth rotational motion to the head.

5. The assistive device as defined in claim 4, wherein the head is removably attached to the shaft and wherein the scrub brush is removably attached to the head via at least one of a friction fit, adhesive hook-and-loop fabric, and magnetic attraction.

6. The assistive device as defined in claim 1, further including a vacuum source in the housing to provide a negative pressure in the scrub brush to assist with fixation of impurities removed from the medical component by the scrub brush.

7. The assistive device as defined in claim 1, further including an ultrasonic pulse generator for providing ultrasonic pulses to the scrub brush during cleansing.

8. The assistive device as defined in claim 1, wherein the medical component is a catheter hub, and wherein the scrub brush is shaped to fit around an end and sides of the catheter hub such that the scrub brush can physically engage external and internal surfaces of the catheter hub.

9. The system as defined in claim 1, wherein the walls of the at least one head remain unbent while cleansing the medical component.

10. A system for cleansing a medical component, comprising:
a scrub brush including walls enclosing a majority of an insert and a cleansing substance;
a handheld assistive device including a receptacle to removably receive the scrub brush so that the medical component can be placed into contact with the insert, wherein the receptacle includes walls that are in contact with and surround a majority of the walls of the scrub brush when the scrub brush is received in the receptacle, wherein the assistive device selectively moves the scrub brush with respect to the medical component without requiring a user to move the handheld assistive device relative to the medical component in order to cleanse the medical component; and
an ultraviolet light system attached to the handheld assistive device and includes a plurality of ultraviolet-emitting lights facing radially inwardly such that the plurality of ultraviolet-emitting lights can direct ultraviolet light radially inwardly toward the scrub brush and the medical component when the scrub brush is engaged in cleansing the medical component.

11. The system as defined in claim 10, wherein the receptacle is included on a head, the head rotatably attached to a motor of the assistive device via a shaft, the scrub brush including a holder containing the insert, the holder removably received within the receptacle, and wherein the assistive device rotates the scrub brush in a back-and-forth movement.

12. The system as defined in claim 11, further comprising a housing including a switch for activating the motor, a display for depicting information relating to cleansing of the medical component, a shield, and an input component for inputting patient information into the assistive device.

13. The system as defined in claim 12, wherein the scrub brush includes a plurality of compliant fingers disposed within the holder, and wherein the cleansing substance includes at least one of CHG and alcohol.

14. The system as defined in claim 13, further comprising a docking station for operably connecting with the assistive device, the docking station including a charging system for charging a power source of the assistive device, the docking station also configured to receive data stored by the device relating to operation of the device.

15. The system as defined in claim 14, wherein the medical component includes a luer connector of a catheter, wherein the holder of the scrub brush is hexagonal, and wherein the receptacle of the head is hexagonal.

16. The system as defined in claim 15, wherein at least one of a speed, time of operation, number of rotation cycles, and direction of movement of the head can be varied, and wherein the scrub brush includes an RFID chip and wherein the assistive device includes an RFID reader for detecting information included on the RFID chip of the scrub brush.

17. A system for cleansing, comprising:
a scrub brush;
a handheld device including a receptacle to removably receive the scrub brush; and
an ultraviolet light system attached to the handheld device including a plurality of ultraviolet-emitting lights facing radially inwardly such that the plurality of ultraviolet-emitting lights can direct ultraviolet light radially inwardly toward the scrub brush and an item to be cleansed when the scrub brush is received in the receptacle and the scrub brush is engaged in cleansing the item to be cleansed, wherein the item to be cleansed is independent of the scrub brush and ultraviolet light system.

18. The system as defined in claim 17, wherein the handheld device selectively moves the scrub brush with respect to the item to be cleansed without requiring a user to move the handheld device relative to the item to be cleansed in order to cleanse the item.

19. The system as defined in claim 17, wherein the plurality of ultraviolet-emitting lights are connected to an interior of a cylindrical structure, and the cylindrical structure is attached to the handheld device.

20. The system as defined in claim 19, wherein the cylindrical structure is attached to the handheld device such that the cylindrical structure is axially slidable with respect to the handheld device.

* * * * *